United States Patent
Leibfritz (10) Patent No.: US 12,097,018 B2
(45) Date of Patent: Sep. 24, 2024

(54) MEASURING DEVICE AND A METHOD FOR MICROWAVE-BASED INVESTIGATION

(71) Applicant: Rohde & Schwarz GmbH & Co. KG, Munich (DE)

(72) Inventor: Martin Leibfritz, Munich (DE)

(73) Assignee: Rohde & Schwarz GmbH & Co. KG, Munich (DE)

( * ) Notice: Subject to any disclaimer, the term of this patent is extended or adjusted under 35 U.S.C. 154(b) by 1391 days.

(21) Appl. No.: 16/563,536

(22) Filed: Sep. 6, 2019

(65) Prior Publication Data

US 2019/0388001 A1 Dec. 26, 2019

Related U.S. Application Data

(62) Division of application No. 12/995,989, filed as application No. PCT/EP2009/003925 on Jun. 2, 2009, now Pat. No. 10,441,191.

(30) Foreign Application Priority Data

Jun. 2, 2008 (DE) .................. 102008026438.5
Dec. 16, 2008 (DE) .................. 102008062484.5

(51) Int. Cl.
| A61B 5/0536 | (2021.01) |
| A61B 5/0507 | (2021.01) |
| A61B 5/00 | (2006.01) |
| A61B 6/04 | (2006.01) |
| A61B 6/50 | (2024.01) |

(52) U.S. Cl.
CPC .......... *A61B 5/0536* (2013.01); *A61B 5/0507* (2013.01); *A61B 5/682* (2013.01); *A61B 6/0435* (2013.01); *A61B 6/502* (2013.01); *A61B 2562/143* (2013.01)

(58) Field of Classification Search
CPC .................................................... A61B 5/0507
See application file for complete search history.

(56) References Cited

U.S. PATENT DOCUMENTS

| 5,334,141 A * | 8/1994 | Carr .................. A61M 5/16836 600/372 |
| 5,704,355 A | 1/1998 | Bridges |
| 5,829,437 A | 11/1998 | Bridges |

(Continued)

FOREIGN PATENT DOCUMENTS

| DE | 30 20 015 A1 | 12/1980 |
| DE | 35 31 893 A1 | 3/1987 |

(Continued)

OTHER PUBLICATIONS

International Search Report mailed Oct. 28, 2009, issued in corresponding International Application No. PCT/EP2009/003925, filed Jun. 2, 2009.

(Continued)

*Primary Examiner* — Angela M Hoffa
(74) *Attorney, Agent, or Firm* — Christensen O'Connor Johnson Kindness PLLC (57) ABSTRACT

A measuring device comprising a microwave transmitter, a microwave receiver, at least one antenna, and a control device. The control device controls the microwave transmitter and the microwave receiver.

8 Claims, 6 Drawing Sheets

(56) References Cited

U.S. PATENT DOCUMENTS

| | | | |
|---|---|---|---|
| 5,999,836 A * | 12/1999 | Nelson | A61B 5/0091 250/341.7 |
| 6,061,589 A * | 5/2000 | Bridges | A61B 6/0435 600/430 |
| 6,345,194 B1 * | 2/2002 | Nelson | A61B 5/0053 250/341.1 |
| 6,768,925 B2 | 7/2004 | Fenn et al. | |
| 7,122,012 B2 * | 10/2006 | Bouton | H01Q 9/0407 600/587 |
| 7,266,407 B2 | 9/2007 | Li et al. | |
| 7,340,292 B2 * | 3/2008 | Li | A61B 5/05 600/430 |
| 7,427,967 B2 | 9/2008 | Hughes | |
| 7,454,242 B2 * | 11/2008 | Fear | A61B 5/0507 600/407 |
| 7,647,089 B2 | 1/2010 | Bond et al. | |
| 7,725,151 B2 | 5/2010 | van der Weide | |
| 8,050,740 B2 | 11/2011 | Davis et al. | |
| 8,095,204 B2 | 1/2012 | Smith et al. | |
| 2004/0077943 A1 | 4/2004 | Meaney et al. | |
| 2004/0097811 A1 | 5/2004 | Smith et al. | |
| 2006/0241410 A1 | 10/2006 | Fang et al. | |
| 2006/0287596 A1 | 12/2006 | Johnson et al. | |
| 2006/0293597 A1 | 12/2006 | Johnson et al. | |
| 2007/0060816 A1 | 3/2007 | Simpkin | |
| 2007/0073144 A1 | 3/2007 | Simpkin | |
| 2009/0012391 A9 | 1/2009 | Simpkin | |
| 2009/0024026 A9 | 1/2009 | Simpkin | |
| 2009/0309786 A1 | 12/2009 | Stolpman et al. | |
| 2010/0069744 A1 | 3/2010 | Simpkin | |
| 2011/0152664 A1 | 6/2011 | Leibfritz | |
| 2011/0160579 A1 | 6/2011 | Leibfritz et al. | |

FOREIGN PATENT DOCUMENTS

| | | |
|---|---|---|
| DE | 692 31 294 T2 | 11/2000 |
| DE | 10 2006 014 230 A1 | 10/2007 |
| EP | 0 694 282 A2 | 1/1996 |
| EP | 0 804 900 A1 | 4/1997 |
| EP | 1 834 667 A2 | 7/2002 |
| WO | 2005/053531 A2 | 6/2005 |
| WO | 2007/112850 A1 | 10/2007 |

OTHER PUBLICATIONS

International Preliminary Report on Patentability mailed Mar. 24, 2011, issued in corresponding International Application No. PCT/EP2009/003925, filed Jun. 2, 2009.

* cited by examiner

MEASURING DEVICE AND A METHOD FOR MICROWAVE-BASED INVESTIGATION

CROSS-REFERENCES TO RELATED APPLICATIONS

This application is a division of U.S. patent application Ser. No. 12/995,989, filed Feb. 22, 2011, which is the National Stage of International Application No. PCT/EP2009/003925, filed Jun. 2, 2009, which claims the benefit of German Application No. 102008026438.5, filed Jun. 2, 2008, and German Application No. 102008062484.5, filed Dec. 16, 2008, all the disclosures of which are incorporated by reference herein.

FIELD OF DISCLOSURE

Embodiments of the present disclosure relate to a measuring device and a method for microwave-based investigation.

BACKGROUND

Antennas, which are distanced by a large air gap from the object to be investigated, are conventionally used for the microwave-based investigation of objects. This serves to achieve remote-field conditions. An influence of the individual object under investigation on the antennas can be avoided in this manner. However, it is disadvantageous that every material transition causes reflections, which interfere with the investigation.

As an alternative, antennas disposed directly on the object to be investigated are used. However, a coupling then occurs between the object under investigation and the antenna. Accordingly, U.S. Pat. No. 5,704,355 discloses a system for detecting breast cancer, which uses an antenna in direct contact with the breast. The additional disadvantage here is the poor accuracy of positioning of the antenna. Accordingly, the breast can slip relative to the antenna during the investigation.

SUMMARY

The disclosure relates to measuring devices and methods for microwave-based investigation of objects, which achieve a high quality of investigation and a low cost.

In accordance with an aspect of the present disclosure, a measuring device is provided. In an embodiment, the measuring device comprises at least one first antenna arrangement is affixed to an object to be investigated, a microwave transmitter and a microwave receiver, wherein the microwave transmitter transmits a microwave signal by the first antenna arrangement into the object to be investigated or the microwave receiver receives a microwave signal by the first antenna arrangement, and a control device. In an embodiment, the control device is configured to control the microwave transmitter and the microwave receiver, and determine a microwave tomography from a microwave signal received.

In accordance with another aspect of the present disclosure, a measuring device for investigating an object is provided. In an embodiment, the measuring device comprises at least one first antenna arrangement attached to the object to be investigated by gluing or clamping, a control device, and at least a microwave transmitter and a microwave receiver. In an embodiment, the microwave transmitter and the microwave receiver are controlled by the control device in order to transmit a microwave signal via the first antenna arrangement into the object to be investigated or to receive a microwave signal via the first antenna arrangement. The microwave signal is scattered by the object to be investigated, and a microwave tomography is determined from a received microwave signal.

In accordance with another aspect of the present disclosure, a measuring device for investigating an object is provided. In an embodiment, the measuring device comprises a microwave transmitter, a microwave receiver, at least one antenna arrangement and a control device. The first antenna arrangement is attached to an object to be investigated by adhesion or clamping. The control device controls the microwave transmitter and the microwave receiver. The microwave transmitter transmits the microwave signal by the first antenna arrangement into the object to be investigated. Alternatively or additionally, the microwave receiver receives the microwave signal by the first antenna arrangement. Reflections at the transition between the air and the object under investigation are avoided in this manner. Accordingly, a high accuracy is possible.

In accordance with another aspect of the present disclosure, a measuring device is provided. In an embodiment, the measuring device includes a microwave transmitter, a microwave receiver, at least one antenna, a control device and a dielectric extension. The dielectric extension is disposed between the antenna and an object to be examined. The control device controls the microwave transmitter and the microwave receiver. With the antenna and the dielectric extension, the microwave transmitter transmits a microwave signal into the object to be investigated. The object to be investigated scatters the microwave signal. The microwave receiver receives the scattered microwave signal by the antenna and the dielectric extension. The length and the dielectric constant of the dielectric extension in this context are dimensioned in such a manner that the object to be investigated is disposed in the remote field of the antenna. Accordingly, an accurate investigation can be achieved with small dimensions of the measuring device.

In some embodiments, the dielectric extension includes a dielectric constant of $\epsilon>2$, preferably of $\epsilon>3$, by particular preference of $\epsilon>4$. The extension comprises a length from 20 cm to 120 cm, preferably from 30 cm to 100 cm, by particular preference from 40 cm to 80 cm. Particularly small dimensions of the measuring device can therefore be achieved.

In some embodiments, the dielectric extension provides a laterally disposed microwave absorber. In this manner, interference through lateral scattering of the microwave signals is avoided. In some embodiments, the microwave absorber is made from a strongly attenuating, non-reflecting material. Accordingly, interference from lateral scattering of the microwave signals can be avoided with small dimensions of the measuring device.

In some embodiments, the object to be investigated is a breast of a female patient. The breast can be disposed between the patient and the extension. In some embodiments, substantially no air is disposed between the breast and the extension. Accordingly, a flat breast, largely homogenous in its thickness is achieved. Moreover, a low-reflection transition of the radiation is achieved in this manner. A high accuracy of the measurement is therefore achieved, especially for the detection of breast cancer.

According to some embodiments, one or more of the measuring devices mentioned briefly above may include at least one second antenna arrangement. The first antenna arrangement and the second antenna arrangement can be individual antennas or antenna arrays. Accordingly, a further increase in accuracy can be achieved.

In some embodiments, the microwave transmitter transmits a microwave signal into the object to be investigated by the first antenna arrangement. The microwave receiver then receives the scattered signal by the second antenna arrangement. Alternatively, the microwave transmitter transmits a microwave signal into the object to be investigated by the second antenna arrangement. The microwave receiver then receives the scattered signal by the first antenna arrangement. In this manner, complex signal processing for the separation of signals transmitted by a single antenna and received by the same antenna can be avoided.

In some embodiments, the second antenna arrangement occupies in succession several positions relative to the object to be investigated. Accordingly, a high-sensitivity resolution can be achieved.

DESCRIPTION OF THE DRAWINGS

The foregoing aspects and many of the attendant advantages of the claimed subject matter will become more readily appreciated as the same become better understood by reference to the following detailed description, when taken in conjunction with the accompanying drawings, wherein:

DETAILED DESCRIPTION

The detailed description set forth below in connection with the appended drawings, where like numerals reference like elements, is intended as a description of various embodiments of the disclosed subject matter and is not intended to represent the only embodiments. Each embodiment described in this disclosure is provided merely as an example or illustration and should not be construed as preferred or advantageous over other embodiments. The illustrative examples provided herein are not intended to be exhaustive or to limit the claimed subject matter to the precise forms disclosed.

Figure 1:
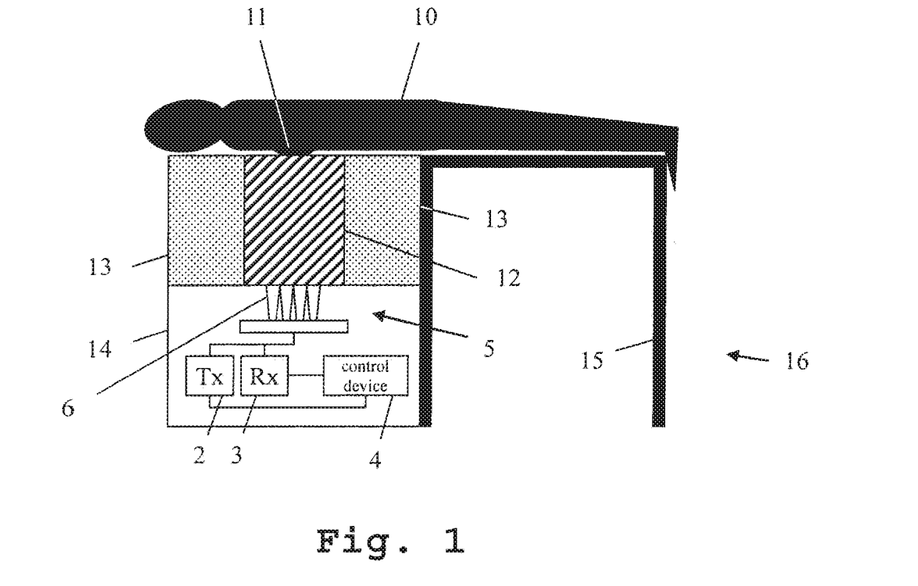
FIG. 1 shows a first embodiment of the measuring device.

FIG. 1 shows a first exemplary embodiment of the measuring device according to the disclosure. A patient 10 is lying in an investigation station 16. In addition to a table 15, the investigation station 16 comprises a housing 14, a dielectric extension 12 and an absorber 13. The housing 14 is disposed below the dielectric extension 12 and the absorber 13. The table 15 is disposed alongside the housing 14, the dielectric extension 12 and the absorber 13. The dielectric extension 12 and the absorber 13 in this context are shown in a cross-sectional presentation.

The breast 11 of the patient 10 is disposed between the rest of her body and the dielectric extension 12 above a first end of the dielectric extension. In this context, the breast 11 is compressed by the body weight of the patient 10. This leads to a largely flat, uniformly thick shape of the breast 11. In this manner, a correction calculation, which eliminates reflections at the surface of the breast, can be implemented in a simplified manner. An upright seated position of the patient 10 or a lying position with the extension 12 placed above are also possible.

The housing 14 contains a microwave transmitter 2, a microwave receiver 3, a control device 4 and an antenna array 5. In this context, the antenna array 5 comprises a plurality of individual antennas 6.

The breast 11 of the patient 10 in this embodiment is the object to be investigated. The control device 4 controls the microwave transmitter 2 in such a manner that the latter transmits a microwave signal by means of the antenna array 5 into the object to be investigated. In this context, the microwave signal is transmitted from the antenna array 5 directly into the extension 12. The extension 12 here provides a high dielectric constant and a low attenuation. In this manner, the effective wavelength of the microwave signal is reduced within the dielectric extension 12. Accordingly, the microwave signal runs through a higher number of wavelengths while it passes through the extension than is the case in a passage through the air. Accordingly, decoupling of the antenna array 5 from the object to be investigated is achieved even at a short distance. That is to say, the antenna properties are not influenced by the properties of the object to be investigated. A decoupling of this kind occurs when remote-field conditions predominate. This is the case, when the microwave signal has covered at least six wavelengths between the antenna 6 and the breast 11.

Using the extension 12 allows the use of high-frequency microwave radiation, without the need to preserve a large distance between the antenna and the object to be investigated.

To avoid interference from microwave signals reflected from the edges of the extension 12, the extension 12 is surrounded by an absorber 13. In this context, the absorber 13 is made from a microwave-absorbing material.

Additional interference from restrictions of the microwave signal at the transition with the air is avoided through the direct contact of the breast 11 on the dielectric extension 12.

The microwave signal is scattered by the object to be investigated, here the breast 11. A part of the scattered microwave signal is scattered through the extension 12 back to the antenna array 5. The microwave receiver 3 is controlled by the control device 4 in such a manner that the former receives the microwave signal scattered back.

In order to achieve as high-sensitivity a resolution as possible within the object to be investigated, different transmission positions and reception positions are used. In this exemplary embodiment, this is achieved by using different individual antennas 6 of the antenna array 5. Finally, the control device 4 determines from the received microwave signals a microwave tomography of the object to be investigated.

Figure 2:
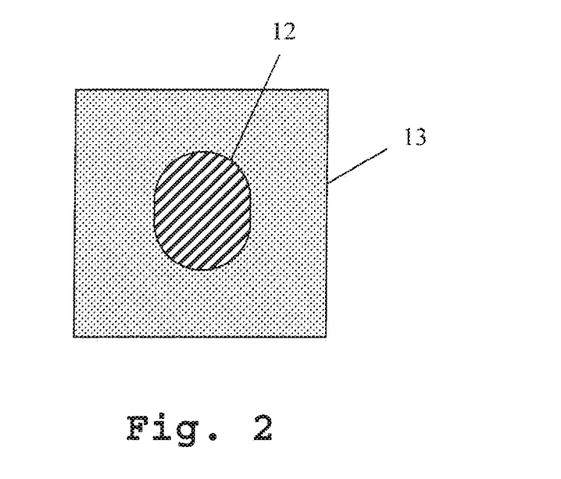
FIG. 2 shows a detail of the first embodiment of the measuring device.

FIG. 2 presents a detail of the first exemplary embodiment of the measuring device according to the disclosure. The drawing shows a sectional view of the dielectric extension 12 and of the absorber 13. In this case, the section passes through the horizontal plane. The form of the extension 12 adapted to the object to be investigated, here the breast 11 of the patient 10, is clearly recognizable. The absorber 13 completely encloses the extension 12 in the horizontal plane. The absorber 13 provides a thickness, which substantially corresponds to the smallest radius of the extension 12. In this manner, a secure absorption of the microwave radiation emitted from the extension 12 is achieved. Interference through reflections is therefore reduced.

Figure 3:
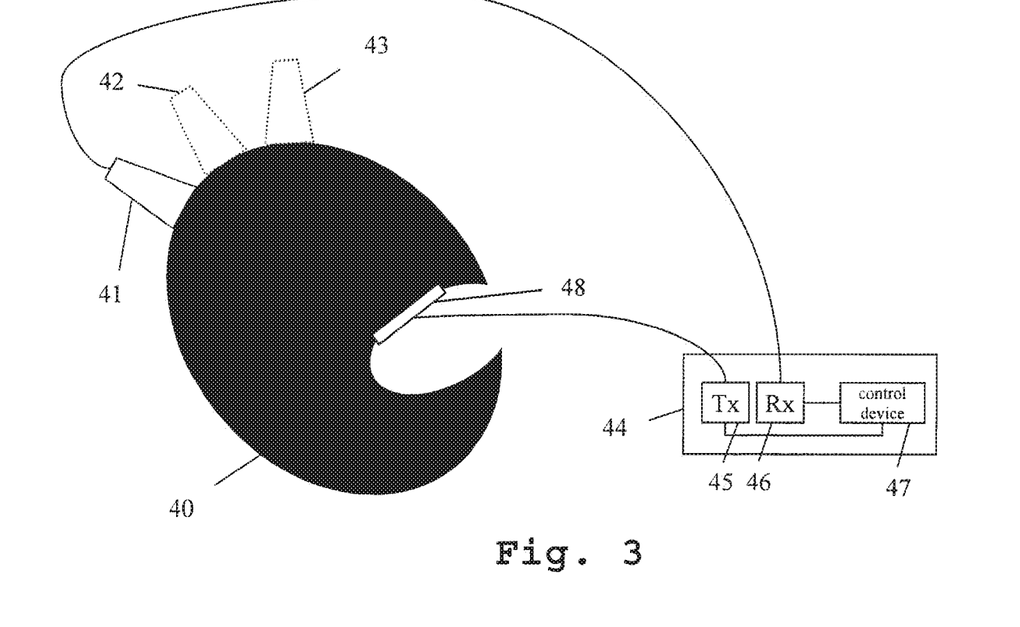
FIG. 3 shows a second embodiment of the measuring device.

FIG. 3 shows a second embodiment of the measuring device according to the disclosure. A housing 44 contains a microwave transmitter 45, a microwave receiver 46 and a control device 47. The control device 47 controls both the microwave transmitter 45 and the microwave receiver 46. The microwave transmitter 45 is connected to an antenna arrangement 48. The antenna arrangement 48 is disposed in a patient's mouth. It is fixed, for example, by an adhesive to the palate in the patient's head 40. In this context, the antenna arrangement 48 is at least partially flexible and can accordingly be adapted to the surface of the palate. The microwave receiver 46 is connected to an antenna 41. The antenna 41 here is in direct contact with the outer side of the patient's head 40. The object to be investigated here is the patient's head 40.

In order to implement an investigation, the control device 47 controls the microwave transmitter 45 in such a manner that it transmits a microwave signal by the antenna arrangement 48 into the patient's head 40. The microwave signal is scattered by the object to be investigated. The scattered microwave signal is received by the microwave receiver 46 by the antenna 41 and rerouted to the control device 47. The antenna 41 adopts several different positions 42, 43 in succession. In this manner, a high-sensitivity resolution is achieved in the investigation. From the scattered signals, the control device 47 determines an at least two-dimensional microwave tomography of the object to be investigated. As an alternative to a re-positioning of the antenna 41, an antenna array can be used.

In this or other embodiments, only very few reflections occur. This is achieved by avoiding air gaps between the antenna arrangement 48 and the patient's head 40 and between the patient's head 40 and the antenna 41. However, the disadvantage with this embodiment is that, because of the small distance, a coupling of the antenna arrangement 48 with the patient's head, and of the antenna 41 with the patient's head 40 occurs. Accordingly, a complex calibration may be needed for every different object to be investigated, that is to say, for every different patient.

As an alternative to the transmission of the microwave signal by the antenna arrangement 48 and the reception of the microwave signal by the antenna 41, a reverse procedure is also possible. In this context, the transmission positions are changed through displacement of the antenna 41 to the several positions 42, 43, and the high-sensitivity resolution is achieved in this manner.

Figure 4:
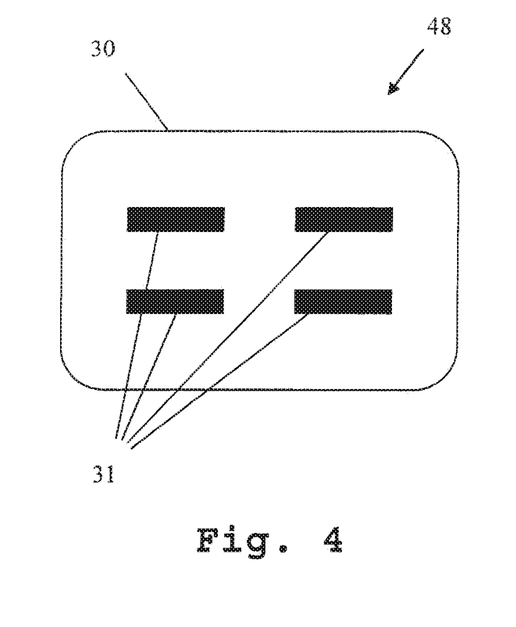
FIG. 4 shows a first detail of the second embodiment of the measuring device.

FIG. 4 provides a first detail of the second embodiment of the measuring device according to the disclosure. The underside, that is to say, the side of the antenna arrangement 48 attached to the palate in FIG. 3, is illustrated here. It contains a flexible carrier 30 and four antenna elements 31. The antenna elements 31 in this context are conductive strips on the underside of the flexible carrier 30.

Figure 5:
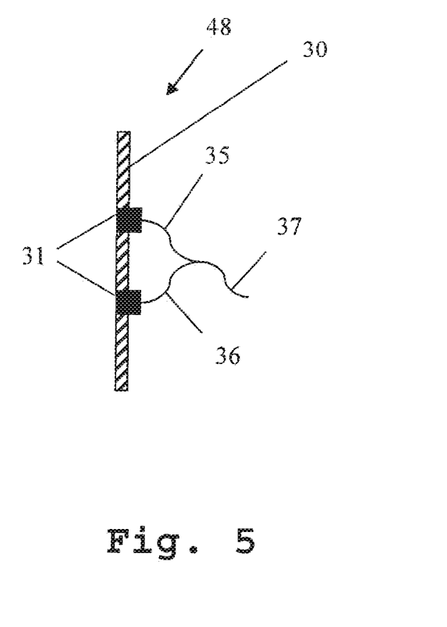
FIG. 5 shows a second detail of the second embodiment of the measuring device.

FIG. 5 shows a second detail of the second embodiment of the measuring device according to the disclosure. Here, the antenna arrangement 48 is shown in a lateral sectional view. The antenna elements 31 are connected on the upper side of the flexible carrier 30 to signal lines 35, 36, which are bundled to form a common signal line 37.

Figure 6:
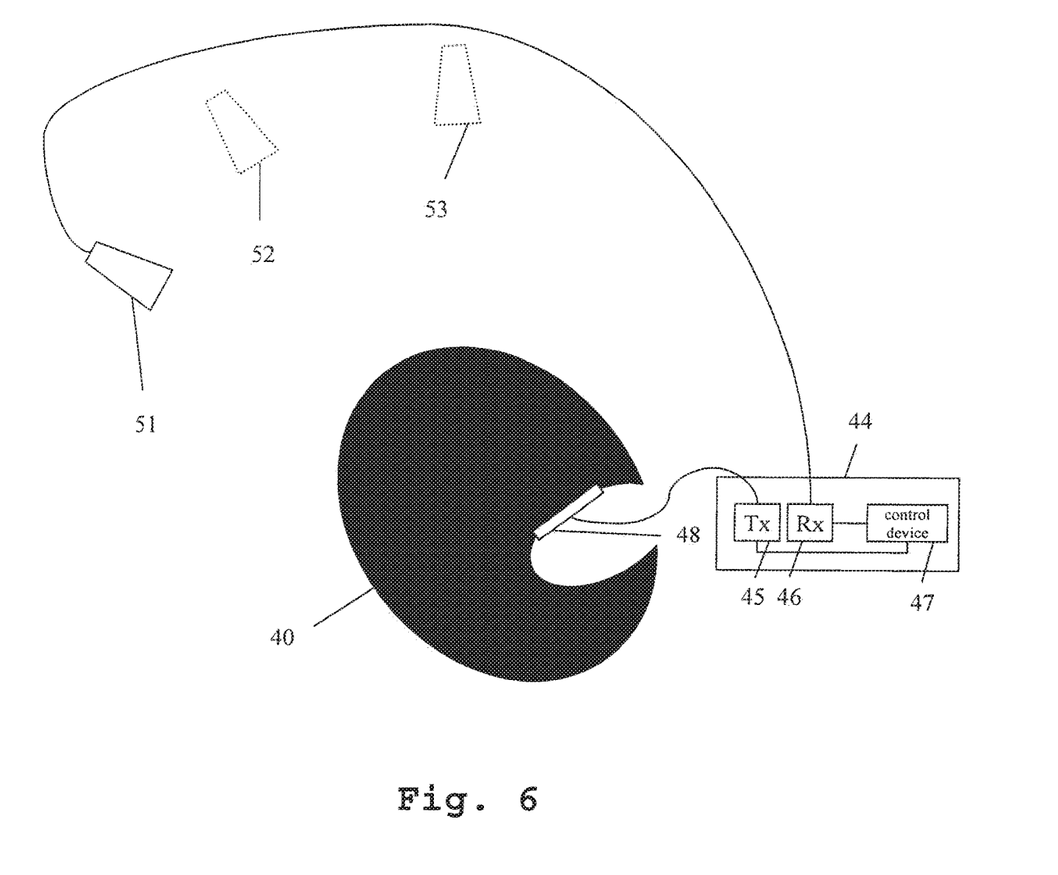
FIG. 6 shows a third embodiment of the measuring device.

FIG. 6 shows a third embodiment of the measuring device according to the disclosure. In order to remove the difficulties caused by the coupling of the antenna 41 and the patient's head 40 explained with reference to FIG. 3, the antenna 51, which corresponds to the antenna 41 from FIG. 3, has not been positioned directly on the patient's head 40. Instead, the antenna 51 provides a spacing distance relative to the patient's head 40. In this context, the spacing distance is selected in such a manner that remote-field conditions predominate.

Otherwise, the embodiment presented here corresponds to the embodiment presented in FIG. 3.

Figure 7:
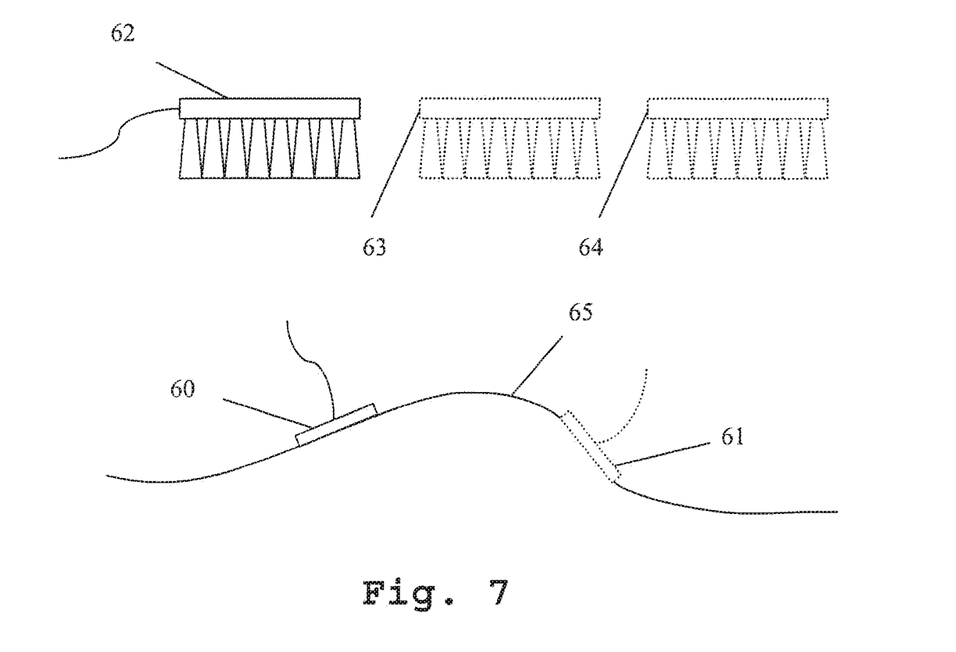
FIG. 7 shows a fourth embodiment of the measuring device.

FIG. 7 shows a fourth embodiment of the measuring device according to the disclosure. The object to be investigated is once again a human breast 65. An antenna arrangement 60 is attached to the breast 65, for example, by gluing. An antenna array 62 is disposed at a spacing distance relative to the breast 65, which guarantees remote-field conditions. In order to implement an investigation, a microwave signal is transmitted into the breast 65 by the antenna arrangement 60. The microwave signal is scattered by the breast 65. The scattered microwave signal is received by the antenna array 62. A microwave tomography of the breast 65 is determined from the received microwave signal by a control device, as presented in FIG. 1, FIG. 3 and FIG. 6. In order to increase the high-sensitivity resolution further, the antenna array 62 is brought in succession into different positions 63, 64. A further increase in the high-sensitivity resolution is achieved by bringing the antenna arrangement 60 to the additional position 61 after the investigation at its original position. A high-sensitivity resolution is achieved through the multiplicity of reception positions and transmission positions.

Through the direct positioning of the antenna arrangement 60 on the breast 65, very low interference through reflections on the skin is achieved. A reversal of the transmission direction is also possible with this embodiment. In this manner, the antenna array 62 is used for transmitting the microwave signal, while the antenna arrangement 60 is used for receiving the microwave signal.

Figure 8:
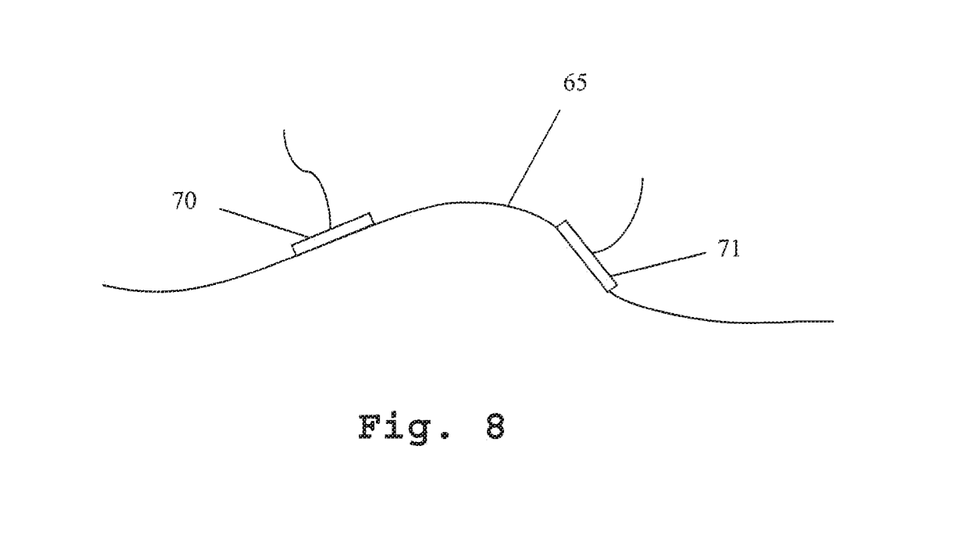
FIG. 8 shows a fifth embodiment of the measuring device.

In FIG. 8, a fifth embodiment of the measuring device according to the disclosure is presented. The exemplary embodiment presented here corresponds in part with the exemplary embodiment presented in FIG. 7. The antenna arrangement 70 corresponds to the antenna arrangement 60 from FIG. 7. Instead of an antenna array 62 from FIG. 7, a second antenna arrangement 71 is used. In this context, the second antenna arrangement 71 is glued like the first antenna arrangement 70 to the breast 65. For the implementation of an investigation, a microwave signal is transmitted by the first antenna arrangement 70 into the breast 65. The microwave signal is scattered by the breast 65. The scattered microwave signal is received by the second antenna arrangement 71. A high-sensitivity resolution is achieved in that every antenna element 70, 71 comprises several individual antennas. An additional increase in the high-sensitivity resolution is possible through the use of additional antenna arrangements. A re-positioning of the only two antenna arrangements 70, 71 also achieves an increase in the high-sensitivity resolution. However, every re-positioning is associated with a positioning inaccuracy.

With this embodiment also, a control device determines a microwave tomography from the received microwave signals, as in FIG. 1, FIG. 3 and FIG. 6. Here also, a reversal of the direction of transmission is possible. Accordingly, the antenna arrangement 71 can also be used for transmitting the microwave signal, while the antenna arrangement 70 is used for receiving the scattered microwave signal.

Figure 9:
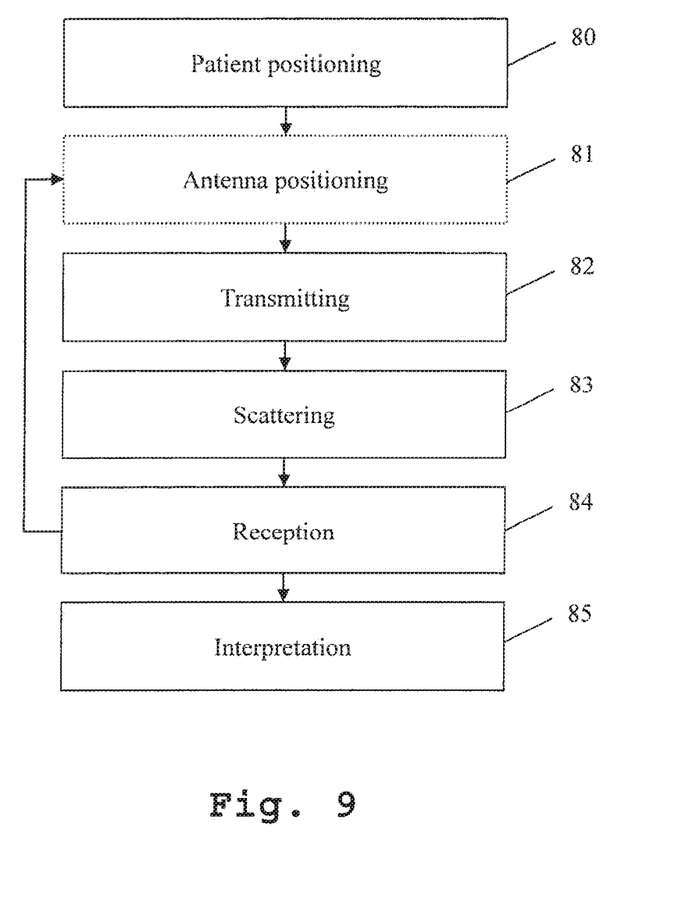
FIG. 9 shows a flow chart of a first embodiment of the method.

FIG. 9 shows a flow chart of a first embodiment of the method according to the disclosure. In a first step 80, the object to be investigated, here, a patient, is positioned. In this context, it is brought into direct contact with the dielectric extension described in detail with reference to FIGS. 1 and 2. In an optional second step 81, the antenna is positioned relative to the object. This step is relevant in the case of movable individual antennas. With the use of an antenna array, the high-sensitivity resolution can be increased by positioning the antenna array at different positions. In a third step 82, a microwave signal is transmitted into the object to be investigated. In a fourth step 83, the microwave signal is scattered by the object to be investigated. In a fifth step 84, the scattered microwave signal is received.

The second step 81 to the fifth step 84 are repeated for different locations within the object to be investigated. The optional second step 81 can be omitted, if the high-sensitivity resolution is achieved through the use of different individual antennas of an antenna array. After the completion of the measurements at all of the locations to be investigated within the object to be investigated, a microwave tomography of the object to be investigated is determined in a sixth step 85.

Figure 10:
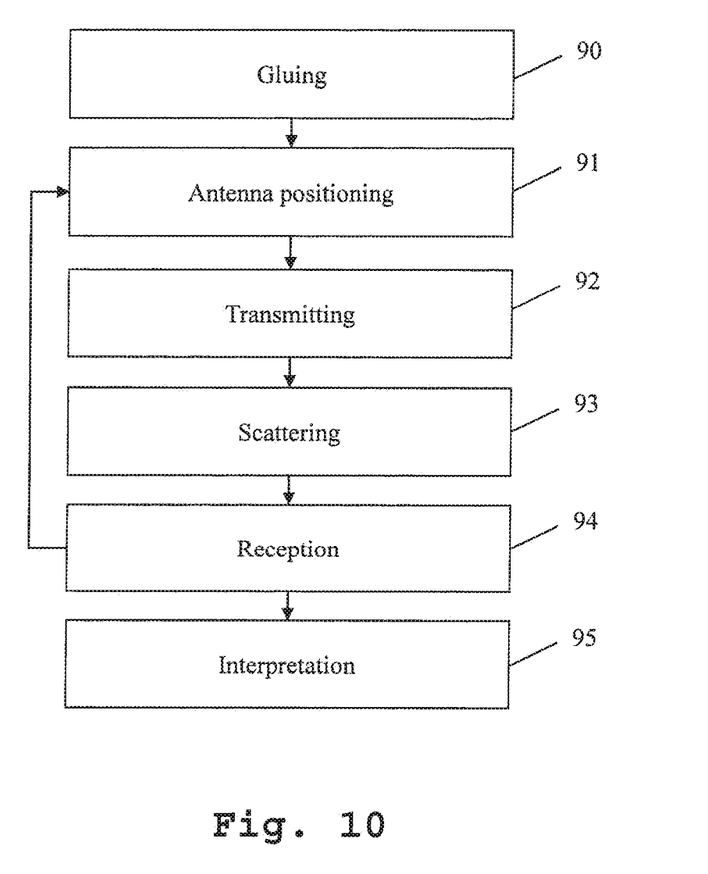
FIG. 10 shows a flow chart of a second embodiment of the method.

FIG. 10 presents a second embodiment of the method according to the disclosure. In a first step 90, an antenna arrangement is attached by, e.g., gluing or clamping, to the object to be investigated. In a second step 91, the object to be investigated, here, a patient, is positioned relative to further antennas or respectively to an antenna array. In a third step 92, a microwave signal is transmitted into the object to be investigated by the antenna arrangement. In a fourth step 93, the microwave signal is scattered by the object to be investigated. In a fifth step 94, the scattered microwave signal is received by the further antennas or respectively by the antenna array.

The second step 91 to the fifth step 94 are repeated for several different locations within the object to be investigated. In this manner, an improved high-sensitivity resolution is achieved. A movement of the further antennas or of the antenna array relative to the object to be investigated can be omitted, if the high-sensitivity resolution is achieved through the use of several different individual antennas of an antenna array. In a sixth step 95, a microwave tomography is produced by the received microwave signals.

A reversal of the signal direction is also possible with this embodiment. For example, the microwave signal can also be transmitted by the further antennas or respectively by the antenna array and received by the antenna arrangement glued in place. The objects to be investigated can be any required objects, especially living or dead human or animal tissue.

The disclosure is not restricted to the exemplary embodiment presented. As already mentioned, different objects can be investigated. The use of different numbers of antennas is also possible. All of the features described above or illustrated in the drawings can be combined with one another advantageously as required within the framework of the disclosure.

The present application may also reference quantities and numbers. Unless specifically stated, such quantities and numbers are not to be considered restrictive, but exemplary of the possible quantities or numbers associated with the present application. Also in this regard, the present application may use the term "plurality" to reference a quantity or number. In this regard, the term "plurality" is meant to be any number that is more than one, for example, two, three, four, five, etc. The terms "about," "approximately," "near," etc., mean plus or minus 5% of the stated value. For the purposes of the present disclosure, the phrase "at least one of A, B, and C," for example, means (A), (B), (C), (A and B), (A and C), (B and C), or (A, B, and C), including all further possible permutations when greater than three elements are listed.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

The embodiments of the invention in which an exclusive property or privilege is claimed are defined as follows:

1. A method, comprising:
    affixing a first antenna to a surface of an object to be investigated, wherein the object to be investigated is a human breast;
    positioning a second antenna and spaced distance from the first antenna and the human breast;
    transmitting a microwave signal from the first antenna into the human breast, the human breast causing the microwave signal to scatter, thereby creating a scattered microwave signal;
    receiving the scattered microwave signal by the second antenna;
    moving the second antenna to another position that is a spaced distance from the first antenna and the human breast; thereafter
    repeating said transmitting a microwave signal from the first antenna into the human breast and said receiving the scattered microwave signal by the second antenna; and
    determining a microwave tomography of the human breast from the received scattered microwave signals.

2. The method according to claim 1, wherein the first antenna and the second antenna are individual antennas or antenna arrays.

3. The method according to claim 1, wherein further comprising moving the first antenna to at least one additional successive position relative to the human breast.

4. The method according to claim 3, wherein the at least one additional successive position of the second antenna includes several additional successive positions relative to the human breast.

5. The method according to claim 1, further comprising adhesively affixing the first antenna to the surface of the human breast.

6. The method according to claim 1, wherein the first antenna is at least partially flexible.

7. The method according to claim 1, further comprising moving the first antenna to at least one successive position relative to the human breast.

8. The method according to claim 1, wherein the at least one second antenna is positioned a spaced distance from the human breast by at least six wavelengths.

* * * * *